United States Patent [19]

Gay et al.

[11] Patent Number: 4,530,250

[45] Date of Patent: Jul. 23, 1985

[54] METHOD FOR SAMPLING SUB-MICRON PARTICLES

[75] Inventors: Don D. Gay, Aiken; William G. McMillan, Ulmers, both of S.C.

[73] Assignee: The United States of America as represented by the United States Department of Energy, Washington, D.C.

[21] Appl. No.: 599,292

[22] Filed: Apr. 12, 1984

[51] Int. Cl.$^3$ .............................................. B01D 50/00
[52] U.S. Cl. .................................... 73/863.12; 55/82; 62/532; 62/55.5; 73/863.21; 73/863.23
[58] Field of Search ..................... 73/28, 432 PS, 863, 73/863.11, 863.12, 863.21, 863.23, 863.25; 62/532, 55.5, 93; 55/80, 82

[56] References Cited

FOREIGN PATENT DOCUMENTS 0912230  3/1982  U.S.S.R. .................................. 55/82

OTHER PUBLICATIONS

*Air Sampling Instruments for Evaluation of Atmospheric Contaminants*, Fifth Edition, 1978, American Conference of Governmental Industrial Hygienists, pp. A5-A9, B6-B10, H1-H9, R9.
Hollander et al., "Sensitive Integrated and Time Resolved Aerosol Measurement by Means of Light Transmission Changes of Metal-Coated Nuclepore Filters (Filter-Fotometer)" *Environ. Sci. & Technol.*, 1981, 15 (4), pp. 471-473.
Farthing, "Particle Sampling and Measurement", *Environ. Sci. & Technol.*, 1982, 16 (4), pp. 237A-244A.
Solomon et al., "Performance Comparison of Three Samplers of Suspended Airborne Particulate Matter"
*Journal of the Air Pollution Controll. Assoc.*, 1982, 32 (4), pp. 373-375.

Primary Examiner—S. Leon Bashore
Assistant Examiner—Andrew J. Anderson
Attorney, Agent, or Firm—Allen F. Westerdahl; Judson R. Hightower

[57] ABSTRACT

Apparatus and method steps for collecting sub-micron sized particles include a collection chamber and cryogenic cooling. The cooling is accomplished by coil tubing carrying nitrogen in liquid form, with the liquid nitrogen changing to the gas phase before exiting from the collection chamber in the tubing. Standard filters are used to filter out particles of diameter greater than or equal to 0.3 microns; however the present invention is used to trap particles of less than 0.3 micron in diameter. A blower draws air to said collection chamber through a filter which filters particles with diameters greater than or equal to 0.3 micron. The air is then cryogenically cooled so that moisture and sub-micron sized particles in the air condense into ice on the coil. The coil is then heated so that the ice melts, and the liquid is then drawn off and passed through a Buchner funnel where the liquid is passed through a Nuclepore membrane. A vacuum draws the liquid through the Nuclepore membrane, with the Nuclepore membrane trapping sub-micron sized particles therein. The Nuclepore membrane is then covered on its top and bottom surfaces with sheets of Mylar ® and the assembly is then crushed into a pellet. This effectively traps the sub-micron sized particles for later analysis.

10 Claims, 7 Drawing Figures

METHOD FOR SAMPLING SUB-MICRON PARTICLES

The United States Government has rights in this invention pursuant to Contract No. DE-AC09-76SR00001 with E. I. duPont de Nemours & Co.

BACKGROUND OF THE INVENTION

This invention relates to a particle collection apparatus and method for sampling sub-micron diameter particles which are airborne.

This invention may be adapted for use as a pollution detection device, as an experimental tool for analyzing particles which have hitherto not been measured accurately, and for scientific measurement of the atmosphere for determining types and sizes of particles contained in jet and rocket exhaust.

It is well-known to use filters to extract particles of greater than one micron diameter from gas samples to be tested. The commonly used glass fiber filters and HEPA filters effectively trap airborne particles having diameters greater than or equal to 0.3 micron. However, these filters are unsuitable for collecting airborne particles of less than 0.3 micron in diameter because such particles exhibit Brownian movement and behave more like gases than particles.

Many attempts have been made to sample particulate matter contained as airborne particles in air. This is especially true where air pollution measurements are desired of smokestack emissions, automobile emissions, jet engine exhaust, dispersion of contaminants from a source of contamination through the atmosphere, and any other gases which are of interest to the researcher. The article, *Air Sampling Instruments For Evaluation Of Atmospheric Contaminants*, Fifth Edition, 1978, American Conference of Governmental Industrial Hygienists, pp. A-5 to A-9, sets forth a variety of methods of sampling for gases and vapors. One typical method which is commonly used is absorption. In this process, a gas sample is bubbled through an absorbing liquid. This is sometimes called a gas washing. Another type mentioned in the article is condensation or freeze-out. This involves a trap immersed in a low temperature bath such as dry ice and acetone or liquid nitrogen. The gas sample is caused to flow through the trap and moisture and other types of contaminants are collected by freezing out or liquefying. It is possible to use a combination of methods with this process for collecting a specific material. The materials thus collected may be analyzed by means of a gas chromatograph or a mass spectrometer. This article, however, does not teach or suggest a specific procedure for obtaining specific sizes of particles, in particular sub-micron diameter particles having a diameter of less than or equal to 0.3 micron. Also, although the use of a trap is suggested in the above article, no specific apparatus is suggested and no particular procedure of obtaining sub-micron sized particles is taught.

Use of metal-coated Nuclepore filters is discussed at some length by the article by W. Hollander, J. Schormann, W. Stober, F. J. Monig, and N. Schwarzer, entitled "Sensitive Integrated and Time-Resolved Aerosol Measurement by Means of Light-Transmission Changes of Metal-Coated Nuclepore Filters (Filter-Fotometer)", *Environ. Sci. & Technol.*, 1981, 15(4), pp. 471-473. This article is incorporated herein by reference. Various types of Nuclepore filters are discussed, and the theory of operation is set forth. Such filters are useful for measuring particulate air pollutants. One type of measurement involves the change in the light transmissivity through the filters caused by aerosol particles deposited therein. There does not appear to be any suggestion of crushing the Nuclepore filter and subjecting it to further processing so as to be able to analyze the sub-micron diameter particles trapped therein, nor is there suggestion of passing particle-laden water therethrough to extract sub-micron diameter particles therefrom.

A variety of types of particle sampling and measurement devices are discussed in W. E. Farthing, "Particle Sampling and Measurement", *Environ. Sci. & Technol.*, 1982, 16(4), pp 237A-244A. Here, a particular apparatus for obtaining a gas sample and analyzing the same is shown. A variety of types of applications for particle sampling devices is discussed in the above article. A variety of sampling methods are discussed, including the hitherto undiscussed inertial sampling methods. Optical methods are also discussed, and other types of particle detection devices are pointed out without elaboration. Nonetheless, the above-identified article does not show a specific type of apparatus used to obtain sub-micron diameter particles. Furthermore, the use of Nuclepore membranes or filters is only discussed broadly and without reference to any specific method or apparatus of obtaining sub-micron diameter particles.

A specific type of experimental procedure employing quartz filters is discussed in the article by P. Solomon, M. Derrick, J. Moyers, and P. Hyde, entitled "Performance Comparison of Three Samplers of Suspended Airborne Particulate Matter", *Journal of the Air Pollution Control Assoc.*, 1982, 32(4), pp. 373-375. In this article, quartz filters are discussed as being used in place of glass fiber filters. A constant air flow or gas flow is maintained through the quartz filters. The filters used then are tested to determine the amount of particulates collected and to determine concentrations of various elements or chemicals which make up the particulate mass. An ethanol solution is used to wet the filters so as to extract particulate matter collected therein. Ion chromatography can then be used to determine the exact composition of the particulate matter in the extraction solution. The extracted solutions can also be analyzed by flame atomic adsorption spectroscopy. However, there is no teaching or suggestion of using another type of apparatus to obtain those particles of sub-micron diameter which ordinarily escape collection by quartz or fiber filters. Also, there is no teaching or suggestion of using a Nuclepore filter to extract particulate matter from gas which has already passed through a quartz or fiber filter.

SUMMARY OF THE INVENTION

It is accordingly one object of the present invention to provide an improved particle collection apparatus which allows collection of airborne particles with diameters less than 0.3 micron which includes a collection chamber cooled by liquid nitrogen, whereby an accurate measurement of the amount of particles by weight carried by air may be accurately measured.

Another further object of the present invention is to provide an improved particle collection apparatus which allows collection of airborne particles with diameters less than 0.3 micron which includes a collection chamber cooled by liquid nitrogen, and forced air circulation, whereby pollutants not previously detectable in air may be accurately collected and the particles identified.

A further object of the present invention is to provide an improved particle collection apparatus which allows collection of airborne particles with diameters less than 0.3 micron, which includes a collection chamber cooled by liquid nitrogen, and forced air circulation, the air being filtered at the entrance to the collection chamber, whereby particles of sub-micron diameter can be detected and identified which otherwise pass through conventional air filters.

A still further object of the present invention is to provide an improved particle collection apparatus which allows collection of airborne particles with diameters less than 0.3 micron, which includes a collection chamber cooled by liquid nitrogen, and forced air circulation, the air being filtered at the entrance to the collection chamber, whereby an accurate measurement of the amount of particles by weight carried by air may be accurately measured.

Another further object of the present invention is to provide an improved particle collection apparatus which allows collection of airborne particles with diameters less than 0.3 micron and includes a collection chamber cooled by liquid nitrogen, and forced air circulation, the air being filtered at the entrance to the collection chamber, moisture and sub-micron diameter particles being frozen in the collection chamber, the frozen ice with the trapped particles being allowed to melt, whereby an accurate measurement of the amount of particles by weight carried by air may be accurately measured.

A still further object of the present invention is to provide an improved method of sampling sub-micron particles which allows collection of airborne particles with diameters less than 0.3 micron and includes a collection chamber cooled by liquid nitrogen, and forced air circulation, whereby an accurate measurement of the amount of particles by weight carried by air may be accurately measured.

A further object of the present invention is to provide an improved method of sampling sub-micron particles which allows collection of airborne particles with diameters less than 0.3 micron and includes a collection chamber cooled by liquid nitrogen, and forces air circulation, the air being filtered at the entrance to the collection chamber, moisture and sub-micron diameter particles being frozen in the collection chamber, whereby particles of sub-micron diameter can be detected and identified which otherwise pass through conventional air filters.

A still further object of the present invention is to provide an improved method of sampling sub-micron particles which allows collection of airborne particles with diameters less than 0.3 micron and includes a collection chamber cooled by a liquid nitrogen, and forced air circulation, the air being filtered at the entrance to the collection chamber, moisture and sub-micron diameter particles being frozen in the collection chamber, the frozen ice with the trapped particles being allowed to melt, the melted liquid then being passed through a capillary pore membrane to trap the sub-micron particles, whereby pollutants not previously detectable in air may be accurately collected and the particles identified.

Another further object of the present invention is to provide an improved sub-micron particle sampler apparatus which allows collection of airborne particles with diameters less than 0.3 micron and includes a collection chamber cooled by liquid nitrogen, forced air circulation, the air being filtered at the entrance to the collection chamber, moisture and sub-micron diameter particles being frozen in the collection chamber, whereby an accurate measurement of the amount of particles by weight carried by air may be accurately measured.

A still further object of the present invention is to provide an improved sub-micron particle sampler apparatus which allows collection of airborne particles with diameters less than 0.3 micron and includes a collection chamber cooled by liquid nitrogen, forced air circulation, moisture and sub-micron diameter particles being frozen in the collection chamber, moisture and sub-micron diameter particles being frozen in the collection chamber, the frozen ice with the trapped particles being allowed to melt, the melted liquid then being passed through a capillary pore membrane to trap the sub-micron particles, whereby pollutants not previously detectable in air may be accurately collected and the particles identified.

The improved sub-micron particle sampler apparatus and method of the present invention comprises a collection chamber cooled by helical coils disposed therein through which flow liquid nitrogen. Particles of greater than 0.3 micron diameter are blocked by a glass fiber filter placed at an air inlet to the collection chamber. As sub-micron sized particles of less than 0.3 micron diameter behave more like gases than like particles due to Brownian motion, freezing the particles into a lattice of ice is an effective way to trap particles. A high volume of air must be sampled in order to obtain good results. Baffles in the collection chamber deflect air over the coils and out an air outlet, the air being driven by an exhaust blower. Moisture frozen from the air collects about the coils, and this ice is then allowed to melt after sufficient air has been sampled. This water is then passed through a Nuclepore membrane to trap particles in the filter. The filter is then covered with Mylar® sheet plastic, or another Nuclepore membrane, to prevent escape of particles. The filter may then be further processed, for example by crushing, ashing, optical analysis, or any other form of analysis desired. If immediate analysis (within a day of filtering) is desired, simply covering with another Nuclepore membrane filter will satisfactorily hold the collected particles. The amounts and nature of the particles trapped may then be determined. The device is useful in the field of pollution testing, as well as in the field of basic atmospheric research. The device will work with any type of gas including atmospheric air.

Further details and advantages of the present invention appear from the following description of a preferred embodiment shown schematically in the drawings.

DETAILED DESCRIPTION OF THE INVENTION

Figure 1:
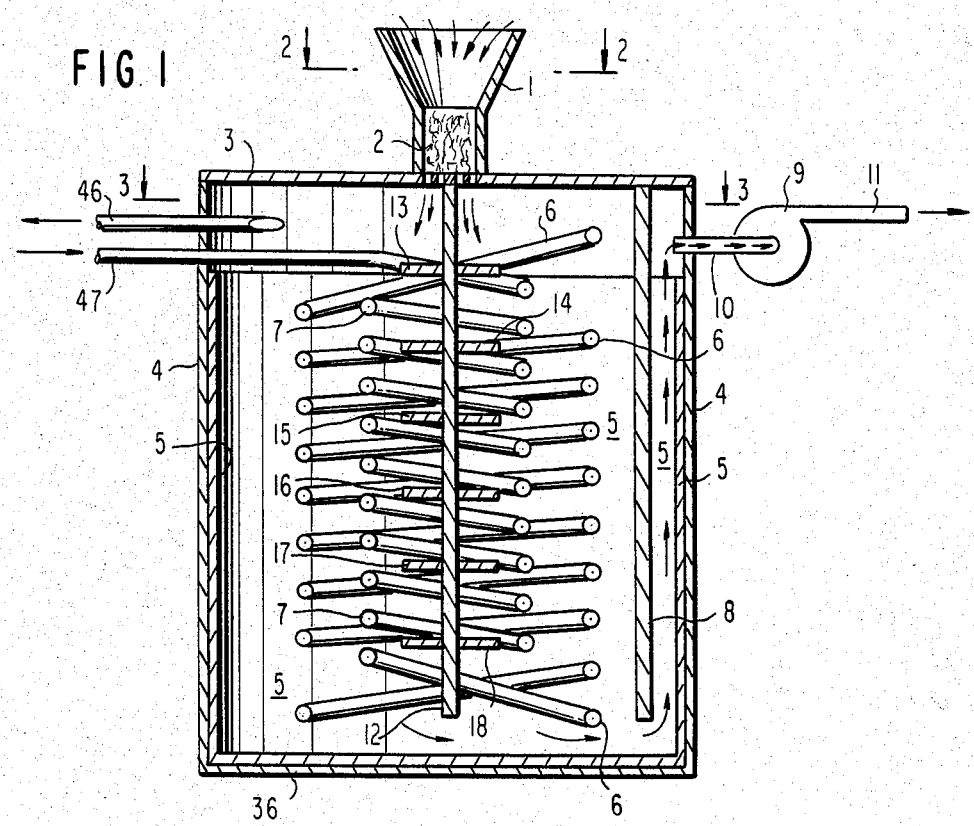
FIG. 1 shows a side sectional view of an apparatus used in the present invention.

FIG. 1 shows a sectional side view of the apparatus in operation. Air is inducted into a high volume sampling head 1. The inducted air is then filtered by a glass fiber filter 2 filling the throat of the high volume sampling head 1.

The glass fiber filter 2 may be a standard HEPA filter or glass fiber filters, which are currently rated as at least 99 percent effective in reducing particle emission. However, that rating is based upon the effectiveness of trapping particles greater than or equal to 0.3 micron in diameter. It is the particles having less than 0.3 micron diameter that pass through the glass fiber filter 2.

The air passing through the glass fiber filter 2 is received in a collection chamber bounded along the top by a removable collection chamber cover 3. The collection chamber cover 3 is supported atop a collection chamber cylindrical sidewall 4 which has a collection chamber bottom wall 36. A flexible collection chamber liner 5 is contained within the collection chamber.

The collection chamber cover 3 is fixedly attached to a deflector baffle support rod 12. The deflector baffle support rod 12 supports a top deflector baffle 13 as well as a plurality of deflector baffles 13–18. The deflector baffles 13–18 act to redirect air flow entering the collection chamber. A baffle plate 8 prevents air entering the collection chamber from directly exiting through an exhaust blower 9. The baffle plate 8 is fixedly connected to the collection chamber cover 3 extending laterally so that either side edge of the baffle plate 8 is adjacent a portion of the collection chamber cylindrical sidewall 4.

A gap is left between the lowermost edge of the baffle plate 8 and the collection chamber bottom wall 36. This arrangement permits air entering the collection chamber to pass across the deflector baffles 13–18 to be deflected thereby, the air then passing beneath the baffle plate 8 and up along the collection chamber cylindrical sidewall 4 until it enters an exhaust blower air inlet line 10. The exhaust blower air inlet line 10 communicates with the suction end of the exhaust blower 9, which causes air to be discharged by an exhaust blower air outlet line 11.

The collection chamber has a flexible collection chamber liner 5 therein which contacts the collection chamber cylindrical sidewall 4 and the collection chamber bottom wall 36. The flexible collection chamber liner 5 is removable from the collection chamber when the collection chamber cover 3 has been removed together with the deflector baffle support rod 12 and the baffle plate 8.

The collection chamber cylindrical sidewall 4 has a pair of orifices therein to admit a liquid nitrogen inlet tube 47 and a gaseous nitrogen outlet tube 46. Although liquid and gaseous nitrogen are referred to, the liquid nitrogen inlet tube 47 and the gaseous nitrogen outlet tube 46 can carry air or other fluids as well. The liquid nitrogen inlet tube 47 communicates with an inner condensing coil 7, which is curved in a helical shape so as to conduct liquid to the bottom of the helical inner coil where the inner coil is connected to an outer condensing coil 6. The outer condensing coil 6 is helical as well and extends to the upper part of the collection chamber, at which point the outer condensing coil 6 communicates with the gaseous nitrogen outlet tube 46.

The inner condensing coil 7 and the outer condensing coil 6 are separately supported within the collection chamber and are not supported by the collection chamber cover 3. Any known support means may be used, for example an insulating support could be used to support the weight of the outer condensing coil 6 and the inner condensing coil 7 above the collection chamber bottom wall 36. Alternatively, the inner condensing coil 7 and the outer condensing coil 6 may be supported by cantilever action from the liquid nitrogen inlet tube 47 and the gaseous nitrogen outlet tube 46. In still another arrangement, external support struts could pass through the collection chamber bottom wall 36 or the collection chamber cylindrical sidewall 4 or both. Such struts would then be adapted for structurally supporting the weight of the inner condensing coil 7 and the outer condensing coil 6.

The flexible collection chamber liner 5 is shown as extending only to the height of the liquid nitrogen inlet tube 47, however the flexible collection chamber liner 5 may extend above the collection chamber cylindrical sidewall 4 provided that an aperture be provided in appropriate locations through the flexible collection chamber liner 5 for the gaseous nitrogen outlet tube 46, the liquid nitrogen inlet tube 47, and the exhaust blower 9.

The deflector baffle support rod 12 is fixedly connected to the collection chamber cover 3, although perforations exist in the collection chamber cover 3 directly below the glass fiber filter 2 so as to permit passage of air from the glass fiber filter 2 into the collection chamber through the collection chamber cover 3. The perforations in the collection chamber cover 3 are sufficiently large to admit air readily, but are not so large as to significantly weaken the collection chamber cover 3 to the point where it could not support the weight of the deflector baffle support rod 12, the deflector baffles 13–18, and the baffle plate 8. The baffle plate 8 is vertically suspended from the collection chamber cover 3 in the present preferred embodiment. Nonetheless, many other support arrangements for the baffle plate 8 may be used, including support struts connecting the uppermost portion of the collection chamber cylindrical sidewall 4 to the baffle plate 8 in a cantilever support arrangement.

The collection chamber must be airtight, and therefore the apertures in the collection chamber cylindrical sidewall 4 for the gaseous nitrogen outlet tube 46, the liquid nitrogen inlet tube 47, and the exhaust blower air inlet line 10 preferably have gaskets, a sealant compound, or the like for preventing entry of unfiltered air into the collection chamber. Thus, there are no apertures permitting entry anywhere in the collection chamber cylindrical sidewall 4 or the collection chamber cover 3 other than through the high volume sampling head 1 and the glass fiber filter 2. In particular, the base of the high volume sampling head 1 is completely sealed to the collection chamber cover 3 so that unfiltered air does not leak into the collection chamber between the high volume sampling head 1 and the collection chamber cover 3.

The parts described hereinabove may be formed of any known materials. For example, the high volume sampling head 1, the collection chamber cover 3, the collection chamber cylindrical sidewall 4, the collection chamber bottom wall 36, as well as all coils and tubes, and the baffle plate 8 may be formed of steel, cast iron, copper, ceramic material, plastic including cellulose plastics, modified vinyls, vinyl resins, the copolymers of vinyl resins, polyethylene, polypropylene, or polyolefin resins. For the tubng and coils, a good heat conducting material is preferably used, for example copper, steel, nickel, or any other type of metal or alloys of metals which are good heat conductors. Nonetheless, even insulating materials may be used for the tubing and coils although such is not the preferred embodiment. The collection chamber cover 3, the collection chamber cylindrical sidewall 4, and the collection chamber bottom wall 36 are in a preferred embodiment formed of materials having insulating properties, for example plastic materials, wood, ceramic materials, or the like. The baffle plate 8 may be made of any material since it is completely enclosed within the collection chamber and merely serves to deflect air flow. Likewise, the exhaust blower air inlet line 10 may be formed of any material, since any air coming in contact with it will be quickly withdrawn by the exhaust blower 9.

The top deflector baffle 13 and the deflector baffles 13–18 are preferably circular and are fixedly attached to the deflector baffle support rod 12 by welding, gluing, riveting, tongue-and-groove joints, or the like. Each of the top deflector baffle 13 and deflector baffles 13–18 are preferably circular and arranged in parallel so as to deflect air flow from the high volume sampling head 1 outward and onto the inner condensing coil 7 and the outer condensing coil 6. However, any type of deflector baffles may be used including conical, perforated plates, ridged plates, cone shapes flaring outward in the direction of expected air flow, or any other known shapes to prevent air from occupying the central portion of the collection chamber exclusively. Although the deflector baffles are shown in FIG. 1 as being generally parallel with the collection chamber bottom wall 36, the top deflector baffle 13 and the deflector baffles 13–18 may be attached to the deflector baffle support rod 12 at an angle other than 90 degrees. Thus, each of the deflector baffles may be sloped, either in the same direction or in all different directions. Each of these arrangements are contemplated to be within the scope of the present invention.

Although circular tubing and coils are shown, any tubing cross-section may be used including ribbed inner wall tubing to enhance convective heat transfer, ribbed outer wall tubing to enhance heat convection transfer, oval cross-sectional inner or outer diameters of tubing, polygonal outer or inner cross-sectional tubing, or any other type of fluid conduit having any known geometric shape either for its outer diameter or for its inner passageway for conducting fluid. Also, although helical coils are used, any type of coil arrangement may be made including square-shaped coils having sharp angles, oval-shaped coils, or the like. Furthermore, instead of the present coil arrangement a radiator-type arrangement could be used having a common header at the top and being connected to permit circulation of coolant fluid within the radiator assembly so as to cool attached fins. Thus, finned tubes are also contemplated within the scope of the present invention although such is not the present preferred embodiment.

Similarly, although a cylindrical collection chamber is shown, any container shape may obviously be used. Similarly, the collection chamber cover 3 and the collection chamber bottom wall 36 need not be flat but may have any shape so long as they make an airtight seal with the sidewalls. Nonetheless, in the preferred embodiment the collection chamber is generally a cylindrical enclosure for economy of materials as well as economy of fabrication and ease of use.

Figure 2:
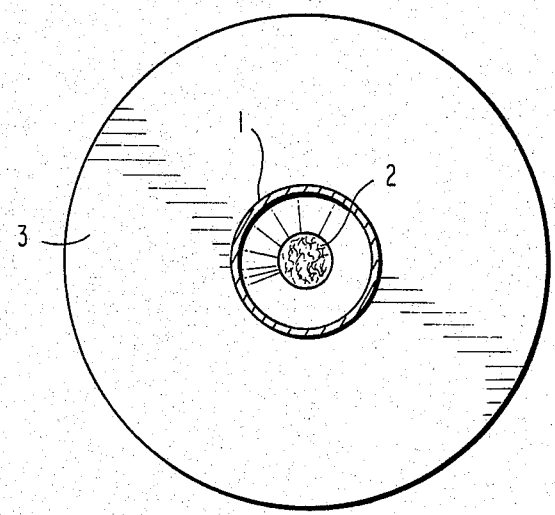
FIG. 2 is a top view partially in section taken along the line 2—2 of FIG. 1.

FIG. 2 is a top view in cross-section along the line 2—2 of FIG. 1. The cylindrical top wall of the high volume sampling head 1 is clearly shown in section in FIG. 2.

The glass fiber filter 2 is circular in top view so that it forms a generally cylindrical body for trapping particles from the air. The filter 2 does not have to be cylindrical; it can be square, rectangular, or any other shape as well. The collection chamber cover 3 also is circular and is generally disc-like since it has a uniform, relatively thin, thickness.

Figure 3:
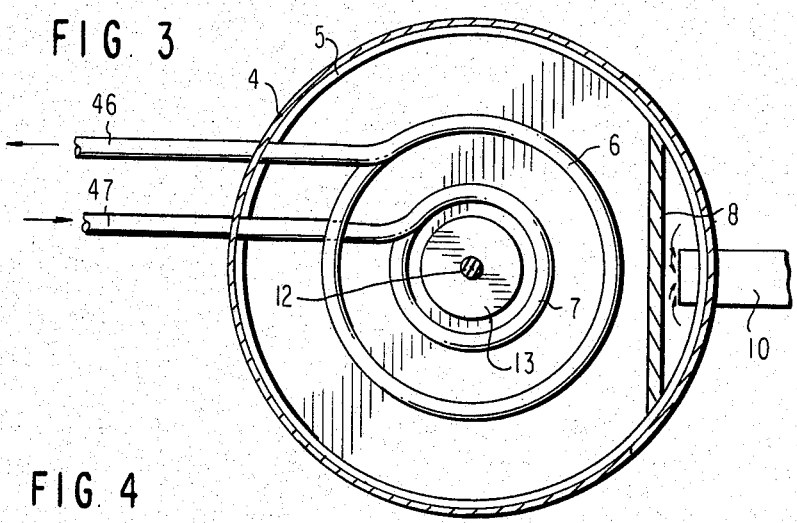
FIG. 3 is a view taken partially in section along the line 3—3 of FIG. 1, and shows the coils and baffle plate.

FIG. 3 is a top view partially in section taken along 3—3 of FIG. 1. The section of the collection chamber cylindrical sidewall 4 is shown to be circular in FIG. 3.

Also, the flexible collection chamber liner 5 top edge is seen clearly in FIG. 3. The flexible collection chamber liner 5 may be a relatively thick, flexible plastic material or even rubber which preferably is self-supporting in the arrangement shown in FIGS. 1 and 3. Nonetheless, even with a much thinner flexible material such as plastic or rubber for the flexible collection chamber liner 5, the top edge of the flexible collection chamber liner 5 may be attached to the collection chamber cylindrical sidewall 4 by pressure-sensitive adhesive, rivets, strut-like supports fixedly attached to an uppermost region of the collection chamber cylindrical sidewall 4, or any other known type of retaining means for retaining the flexible collection chamber liner 5 to the collection chamber cylindrical sidewall 4.

Also as seen in FIG. 3, the baffle plate 8 extends such that air is not permitted to pass between the flexible collection chamber liner 5 and either of the side edges of the baffle plate 8, so that air must be deflected through the collection chamber, under the lowermost edge of the baffle plate 8 and above the collection chamber bottom wall 36 such that it is drawn completely along the length of the inner condensing coil 7 and the outer condensing coil 6 before being withdrawn by the exhaust blower air inlet line 10.

The outer condensing coil 6 is shown in FIG. 3 as integral with the gaseous nitrogen outlet tube 46. Also, the inner condensing coil 7 is shown in FIG. 3 as being integral with the liquid nitrogen inlet tube 47. The top deflector baffle 13 is shown as having a circular periphery. Also, the deflector baffle support rod 12 is shown in FIG. 3 as having a circular cross-section. The inner condensing coil 7 and the outer condensing coil 6 each are seen as having a circular shape in top view in FIG. 3, nonetheless the inner condensing coil 7 and the outer condensing coil 6 are actually helically-shaped and extend downward into the collection chamber seen in FIG. 3. The bottom of the collection chamber is shown as covered with the flexible collection chamber liner 5 in FIG. 3.

Figure 4:
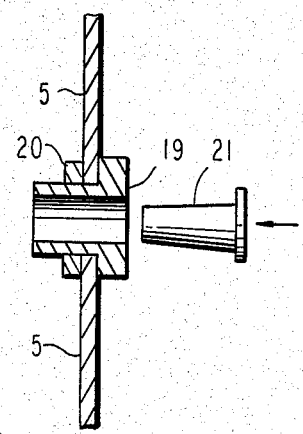
FIG. 4 is a side sectional view of a coupling passing through a flexible inner bag which can be plugged.

FIG. 4 is a side view in section of the flexible collection chamber liner 5 having an outlet port therein for drainage of liquid collected in the flexible collection chamber liner 5. A plug 21 is shown for insertion into a female coupler element 19.

The plug shown in FIG. 4 is fixed in leak-tight arrangement with the flexible collection chamber liner 5. The female coupler element 19 has a cylindrical central opening therein for passage of fluid therethrough and for receiving the coupler plug 21. An abutment portion on the female coupler element 19 contacts the flexible collection chamber liner 5 and is glued or adhered to the flexible collection chamber liner 5 at the juncture thereof.

An additional liquid seal is formed by the annular coupler element 20 having an annular opening therein sized to snugly receive the projecting cylindrical portion of the female coupler element 19. A flat portion of the annular coupler element 20 contacts the flexible collection chamber liner 5 and may be glued or adhered thereto. The annular coupler element 20 may also be glued, welded, or otherwise adhered to the cylindrical portion of the female coupler element 19 so as to retain the two parts together to form a fluid-tight seal.

Figure 5:
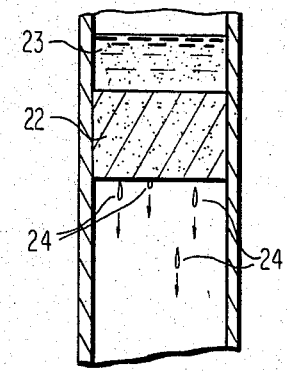
FIG. 5 is a schematic diagram of the passage of water through a Nuclepore membrane.

FIG. 5 is a schematic drawing of a Buchner funnel having a polycarbonate capillary pore membrane filter 22 therein for filtration of collected liquid 23 from the collection chamber. Particulate matter is shown as dots in the unfiltered collected water 23 in FIG. 5. Passing through the polycarbonate capillary pore membrane filter 22 in FIG. 5 is filtered water 24. The filtered water 24 is to be discarded, and the polycarbonate capillary pore membrane filter 22 is saved for further processing and analysis of the trapped particles.

Figure 6:
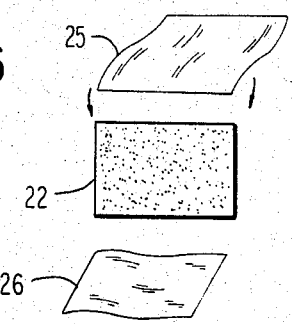
FIG. 6 is a schematic diagram of the Nuclepore membrane being covered at its top and bottom by Mylar ® sheets.

FIG. 6 is a schematic view of the polycarbonate capillary pore membrane filter 22 removed from the Buchner funnel to be placed upon a Mylar ® film sheet bottom membrane filter cover 26, and then to be covered by a Mylar ® film sheet top membrane filter cover 25. The Mylar ® film sheet bottom membrane filter cover 26 and the Mylar ® film sheet top membrane filter cover 25 are used to prevent escape of the particles from the polycarbonate capillary pore membrane filter 22 since the particles are sufficiently small to behave as a gas. If the particles trapped on the Nuclepore membrane are to be determined or analyzed immediately, the Mylar ® can effectively be replaced with additional Nuclepore membrane filters, like that used to filter. The pore sizes will be the same and no loss of trapped particles would be anticipated. The Nuclepore probably could not be compressed into a pellet, though, therefore other types of analysis would be appropriate that do not require compressing the filter into a pellet.

Figure 7:
FIG. 7 is a view of the crushed Nuclepore membrane shown in perspective.

FIG. 7 is a perspective view of the polycarbonate capillary pore membrane filter 22 crushed to pellet size for further processing as by ashing or wet digestion for further determination of the amount, character, and nature of the particles trapped therein.

In operation, air is drawn into the high volume sampling head 1 and is filtered by the glass fiber filter 2. Other kinds of filters may be used if desired, so long as such filter is capable of effectively trapping those airborne particles having diameter sizes greater than or equal to 0.3 micron.

The filtered air leaving the glass fiber filter 2 passes through apertures in the collection chamber cover 3 and enters the collection chamber. The air is deflected by the top deflector baffle 13 as well as all of the deflector baffles 13-18 so as to flow around the inner condensing coil 7 and the outer condensing coil 6.

Liquid nitrogen is used to cool the collection chamber by passage in the liquid nitrogen inlet tube 47, through the inner condensing coil 7, then through the outer condensing coil 6 where it is outletted as gaseous nitrogen through the gaseous nitrogen outlet tube 46. Since liquid nitrogen boils at a low temperature, the inner condensing coil 7 and outer condensing coil 6's surfaces becomes sufficiently cold to freeze moisture from the air as ice onto the outer surfaces of the inner condensing coil 7 and the outer condensing coil 6.

In order to collect sufficient moisture for making a valid sample, a very high volume of air must be employed. Particles having diameters of less than 0.3 micron are frozen with the moisture in the air as ice which collects along the outer surfaces of the tubes.

When a sufficient amount of ice has collected, the air flow is stopped and the collection chamber allowed to warm. Warming and liquefication of the ice collected on the outer surfaces of the inner condensing coil 7 and the outer condensing coil 6 may be accomplished by passage of air in the liquid nitrogen inlet tube 47, through the inner condensing coil 7, to the outer condensing coil 6, and out the gaseous nitrogen outlet tube 46. As the ice melts, it is collected as liquid water within the flexible collection chamber liner 5. Due to the tendency of sub-micron sized particles to diffuse into the air, and due to the Brownian movement of the particles as they behave somewhat like gaseous compounds, the liquid collected in the flexible collection chamber liner 5 is maintained in a chilled condition so as to reduce the escape of the sub-micron sized particles. Thus, the sub-micron sized particles having been trapped within an ice lattice and the liquefied, an effective trap for this type of particle is achieved. Such particles are not effectively trapped by conventional methodologies used for larger particles. Thus, the present invention brings about the concentration of these sub-micron sized particles by reducing their diffusion and Brownian movements and then locking them in place in the ice lattice formed by the freezing-out of water vapor present in the air.

Although liquid nitrogen is used, low temperatures may be achieved by use of other liquefied gases, for example dry ice and acetone, or liquid oxygen, or the like may be used and will effectively separate the vapors from air causing the concentration effect within the super-cooled collection chamber as discussed in the above by reducing the diffusibility and Brownian movement of the gaseous compounds contained in the air.

The baffle plate 8 prevents air from escaping directly from the collection chamber to the exhaust blower air inlet line 10. Thus, after air has passed along the entire length of the inner condensing coil 7 and the outer condensing coil 6, it is then drawn toward the other side of the baffle plate 8 and up along the collection chamber cylindrical sidewall 4 and into the exhaust blower air inlet line 10. The air is exhausted from the collection chamber by the exhaust blower air inlet line 10 and is then forced out under pressure through the exhaust blower air outlet line 11. As discussed above, following collection of sufficient ice and melting of the ice in a separate operation, the collection chamber cover 3 is removed together with the deflector baffle support rod 12 and deflector baffles 13-18 as well as the baffle plate 8.

Next the inner condensing coil 7 and the outer condensing coil 6 are removed as a unit by lifting upwards and out of the collection chamber. This is facilitated by removal of the liquid nitrogen inlet tube 47 and the gaseous nitrogen outlet tube 46 as by threaded or glued couplings located within the collection chamber. Alternatively, the collection chamber cylindrical sidewall 4 may be slotted above the apertures receiving the gaseous nitrogen outlet tube 46 and the liquid nitrogen inlet tube 47. The slots then extend all the way to the top edge of the collection chamber cylindrical sidewall 4 to permit sliding movement upward of the liquid nitrogen inlet tube 47 and the gaseous nitrogen outlet tube 46 together with the inner condensing coil 7 and the outer condensing coil 6. In such an embodiment, the slots would need to be temporarily sealed as by a rubber membrane or the like to prevent passage of unfiltered air into the collection chamber.

The coupler plug 21 remains in sealing engagement in the female coupler element 19 throughout the cooling and warming operations. After removal of the portions of the apparatus discussed in the above, the flexible collection chamber liner 5 is then removed and closed. The closure may be a twist-tie wire closure member, or a tongue-and-groove arrangement may be provided on the flexible collection chamber liner 5 itself to form a closure means therein, such closure means being used on common plastic bags as used in the kitchen for storage of food and the like.

The closed flexible collection chamber liner 5 is them removed and placed for storage if desired in a chilled, insulated receptacle being surrounded by an ice bag to prevent escape of the sub-micron sized particles into the air.

During the cooling operation of the collection chamber itself, the exterior of the collection chamber cylindrical sidewall 4 may be insulated or the entire collection chamber itself may be received within a receptacle having a low thermal conductivity, so as to enhance the energy efficiency of the overall process by avoiding the necessity of using excessive amounts of liquid nitrogen for cooling the air.

When ready for testing, the unfiltered collected water 23 as shown in FIG. 5 is passed through a Buchner funnel and through a polycarbonate capillary pore membrane filter 22. The sub-micron sized particles are trapped within the polycarbonate capillary pore membrane filter 22. The filtered water 24 leaving the polycarbonate capillary pore membrane filter 22 is free of the sub-micron sized particles. The filtered water 24 is then discarded, and as shown in FIG. 6 the polycarbonate capillary pore membrane filter 22 is covered on its top by the Mylar® film sheet top membrane filter cover 25 and is covered on its bottom by the Myler® film sheet bottom membrane filter cover 26. This effectively prevents escape of the sub-micron sized particles from the polycarbonate capillary pore membrane filter 22.

The Buchner funnel is used by attachment to a vacuum maintained at less than 10 p.s.i. to draw the water through the capillary pore filter, as is well-known. The covered polycarbonate capillary pore membrane filter 22 is indicated in FIG. 6 may then be processed by examination using, for example, spectrographic analysis, light absorption characteristics, radioanalytical techniques, or other conventional analytical techniques.

When the polycarbonate capillary pore membrane filter 22 is crushed to a pellet as shown in FIG. 7, escape of the sub-micron sized particles is effectively inhibited and this allows storage of the pellet until appropriate testing can be conducted. The pellet may also be processed by ashing or wet digestion for subsequent analysis of desired chemical compounds or elements. Such analysis techniques may be any conventional or known analytical techniques.

As shown in the foregoing, the apparatus of the present invention samples those particles normally missed by using the standard HEPA filters or glass fiber filters. Thus, vital but missing data can be supplied in determining the total emission load the emissions source is adding to the environment. These above-mentioned standard filters are rated as at least 99 percent effective in reducing particle emissions, but that rating is based upon the effectiveness of trapping particles greater than or equal to 0.3 microns in diameter. The present invention apparatus and method will re-define collection efficiencies of the standard filters.

Because of the possible magnitude of this unknown area of sub-micron particles, the present invention may serve as a stimulus in the development of better filtration methods and/or filters, as well as a stimulus in the basic research of the long-term transport and physicochemical interactions of these particles in the atmosphere. Such will also serve as a stimulus for a better understanding of the effect of these particles in an on various biological and environmental systems.

The present invention apparatus and method will also serve as a quality control mechanism in determining the efficiency of various trapping methods and procedures aimed at reducing the total amount of particles exiting an emissions stack.

The apparatus and method for sampling of submicron sized particles of the present invention is capable of achieving the above-enumerated objects and while preferred embodiments of the present invention have been disclosed, it will be understood that it is not limited thereto but may be otherwise embodied within the scope of the following claims.

What is claimed is:

1. A method for sampling sub-micron sized particles, comprising:

passing a volume of air through a filter which effectively traps airborne particles having diameters of greater than or equal to 0.3 micron;

chilling the air to a cryogenic temperature in a collection chamber so that moisture in the air freezes out trapping sub-micron sized particles in an ice lattice;

exhausting the air from the collection chamber;

melting the ice into a chilled liquid;

passing the liquid through a filter which is capable of removing sub-micron sized particles from the liquid;

whereby samples of sub-micron sized particles are collected.

2. The method for sampling particles as claimed in claim 1, further comprising:

introducing a liquefied gas into a means for cooling the air to cryogenic temperatures;

whereby boiling of the liquefied gas chills the air;

removing the gas which has changed into the vapor phase;

providing baffle plates to direct air flow across said means for cooling;

providing a baffle plate to direct air to the bottom of said collection chamber;

and providing a blower for removing air from said collection chamber.

3. The method for sampling particles as claimed in claim 2, further comprising the steps of:

placing a flexible collection chamber liner within said collection chamber prior to sampling the air;

collecting the liquid in said flexible collection chamber liner;

and removing said flexible collection chamber liner from said collection chamber with said liquid therein;

whereby removal of said liquid is accomplished by transporting said flexible collection chamber liner.

4. The method for sampling particles as claimed in claim 2, wherein said means for cooling includes a helical coil for receiving said liquefied gas;

whereby a liquefied gas is introduced into said coil so as to cool said coil and thereby cool air which is directed across said coil.

5. The method for sampling particles as claimed in claim 4, further comprising the steps of:

providing a collection chamber having a removable top wall;

attaching a support to said top wall;

providing at least a baffle on said support for deflecting air across said means for cooling;

and removing said top wall from said collection chamber to remove said flexible liner from said collection chamber.

6. The method for sampling particles as claimed in claim 2, wherein a Nuclepore membrane is used for filtering sub-micron sized particles from said liquid;

and drawing a vacuum along one side of said Nuclepore membrane while maintaining a supply of said liquid on the other side of said membrane so as to force the liquid through said Nuclepore membrane and trap the sub-micron sized particles within said Nuclepore membrane.

7. The method for sampling particles as claimed in claim 6, wherein said Nuclepore membrane is retained in a Buchner type funnel during the filtration of the liquid.

8. The method for sampling particles as claimed in claim 7, further comprising the steps of covering said Nuclepore membrane to prevent loss of trapped submicron sized particles therefrom; removing said covered Nuclepore membrane from said Buchner type funnel;

and pressing said covered Nuclepore membrane into a pellet that effectively inhibits the loss of trapped particles so as to allow storage;

whereby sub-micron sized particles are trapped within said pellet for further use.

9. The method for sampling particles as claimed in claim 8, further comprising the step of wet ashing said pellet to analyze the sub-micron sized particles trapped therein.

10. The method for sampling particles as claimed in claim 8, further comprising the step of ashing said pellet for subsequent analysis of desired chemical compounds.

* * * * *